(12) United States Patent
Lorcheim et al.

(10) Patent No.: US 12,201,738 B2
(45) Date of Patent: Jan. 21, 2025

(54) SYSTEM FOR CONVERTING AN EXISTING ETHYLENE OXIDE VACUUM STERILIZER INTO A CHLORINE DIOXIDE VACUUM STERILIZER

(71) Applicants: Emily Lorcheim, Califon, NJ (US); Paul Lorcheim, Califon, NJ (US); Kevin Lorcheim, Lebanon, NJ (US)

(72) Inventors: Emily Lorcheim, Califon, NJ (US); Paul Lorcheim, Califon, NJ (US); Kevin Lorcheim, Lebanon, NJ (US)

(73) Assignee: ClorDiSy Solutions, Inc., Branchburg, NJ (US)

( * ) Notice: Subject to any disclaimer, the term of this patent is extended or adjusted under 35 U.S.C. 154(b) by 524 days.

(21) Appl. No.: 17/691,517

(22) Filed: Mar. 10, 2022

(65) Prior Publication Data
US 2023/0050362 A1    Feb. 16, 2023

Related U.S. Application Data

(60) Provisional application No. 63/234,792, filed on Aug. 19, 2021, provisional application No. 63/233,805, (Continued)

(51) Int. Cl.
*A61L 2/20*    (2006.01)
*A61L 2/24*    (2006.01)
(Continued)

(52) U.S. Cl.
CPC .................. *A61L 2/20* (2013.01); *A61L 2/24* (2013.01); *B01D 53/02* (2013.01); *A61L 2101/06* (2020.08); *A61L 2202/11* (2013.01); *A61L 2202/122* (2013.01); *A61L 2202/14* (2013.01); *A61L 2202/23* (2013.01); *A61L 2202/24* (2013.01); *B01D 2253/102* (2013.01); *B01D 2257/204* (2013.01)

(58) Field of Classification Search
CPC ... A61L 2/20; A61L 2/206; A61L 2/24; A61L 2202/11; A61L 2202/122; A61L 2202/14; A61L 2202/24; A61L 2202/15
See application file for complete search history.

(56) References Cited

U.S. PATENT DOCUMENTS 4,436,819 A  3/1984 Manning
4,504,442 A  3/1985 Rosenblatt et al.
(Continued)

*Primary Examiner* — Lessanework Seifu
(74) *Attorney, Agent, or Firm* — Thomas J. Germinario

(57) ABSTRACT

This invention serves to repurpose existing ethylene oxide sterilization chambers utilizing a novel chemical means of sterilization. Ethylene oxide is a longstanding gaseous sterilant for medical devices but has increasing problems associated with its hazards. Ethylene oxide is a carcinogenic and explosive chemical, and its emissions can be very harmful and cause serious health risks. Due to this, the FDA and many medical device manufacturers are trying to reduce or eliminate the use of the gas. Chlorine dioxide gas is a nearly identical alternative mode of sterilization that is non-carcinogenic and non-explosive. If firms choose to eliminate the use of ethylene oxide but do not want to waste the capital expenditure on existing sterilizers, they can instead utilize the ethylene oxide-to-chlorine dioxide conversion system of the present invention and use an effective and environmentally friendly form of sterilization in a system they already possess.

12 Claims, 2 Drawing Sheets

Related U.S. Application Data filed on Aug. 17, 2021, provisional application No. 63/233,782, filed on Aug. 17, 2021, provisional application No. 63/233,484, filed on Aug. 16, 2021.

(51) Int. Cl.
*B01D 53/02* (2006.01)
*A61L 101/06* (2006.01)

(56) References Cited

U.S. PATENT DOCUMENTS

| | | |
|---|---|---|
| 4,681,739 A | 7/1987 | Rosenblatt et al. |
| 5,118,471 A | 6/1992 | Andersen et al. |
| 6,042,802 A | 3/2000 | Drake |
| 6,840,084 B2 | 6/2005 | Nikolskaya |
| 7,776,292 B2 | 8/2010 | Wilson et al. |
| 8,192,684 B2 | 6/2012 | Mason et al. |
| 8,894,936 B2 | 11/2014 | Ozdamar |
| 2007/0292305 A1 | 12/2007 | Dempsey et al. |
| 2008/0286147 A1 | 11/2008 | Wilson et al. |
| 2016/0318992 A1 | 11/2016 | Pomrink et al. |

SYSTEM FOR CONVERTING AN EXISTING ETHYLENE OXIDE VACUUM STERILIZER INTO A CHLORINE DIOXIDE VACUUM STERILIZER

REFERENCE TO PRIOR APPLICATIONS

This application claims the benefit of the filing dates of U.S. Provisional Application Nos. 63/233,484 (filed Aug. 16, 2021), 63/233,782 (filed Aug. 17, 2021), 63/233,805 (filed Aug. 17, 2021), and 63,234,792 (filed Aug. 19, 2021), which are incorporated herein by reference.

FIELD OF INVENTION

The present invention relates to the general field of sterilization equipment, and more specifically to such equipment which uses chlorine dioxide as the sterilizing agent.

BACKGROUND OF THE INVENTION

The present invention is designed to address the need for transforming an existing ethylene oxide sterilizer into a chlorine dioxide gas sterilizer. Although ethylene oxide is currently the principal means of gas sterilization for the medical device industry, many firms are looking to find alternative methods. This trend is due to ever increasing environmental and health issues associated with ethylene oxide. Ethylene oxide is a known carcinogen, and its emissions are believed to have been the cause of numerous incidents of cancer and have resulted in class action lawsuits against industrial sterilization firms which implement ethylene oxide gas methodology. Another factor for medical device manufacturers wanting to limit use of ethylene oxide is the explosive nature of ethylene oxide. This tendency limits the nature of devices that can be sterilized and restricts further product innovation. However, many facilities across the globe already have ethylene oxide sterilizers in place due to its broad usage.

Chlorine Dioxide, on the other hand, is nearly identical to ethylene oxide in its sterilization capabilities, while being non-carcinogenic, non-explosive, and leaving non-detectable amounts of residuals. The challenge is that, in order to introduce a widespread implementation of this mode of sterilization, many gas sterilization chambers would need to be installed causing high capital expenditures and a need to dispose of existing costly ethylene oxide systems. With this present invention, firms can use existing ethylene oxide chambers and repurpose them to become chlorine dioxide gas sterilizers.

SUMMARY OF THE INVENTION

This invention is a module capable of linking to an ethylene oxide vacuum sterilizer in order to convert the sterilizer into a chlorine dioxide gas vacuum sterilizer. The invention is a module that can be wall mounted to be easily adaptable to any facility. Attached to the module are all the necessary components to produce chlorine dioxide gas, monitor the process, document the process as required by regulatory agencies and send the gas into the sterilization chamber. Also included in the present invention is the corresponding Human Machine Interface (HMI) and Process Control System (PCS). The HMI has the ability to store sterilization cycles, display humidity, display chlorine dioxide gas concentration, display vacuum levels, and display accumulated dosage.

The module is a framework that contains all inputs necessary to generate chlorine dioxide and run a vacuum sterilization cycle within an existing chamber. The module receives information through the HMI and/or PCS on the parameters entered in for a sterilization recipe. The module then follows the cycle of producing an environment following the conditions desired and following the necessary time periods per interval in the process. The HMI determines the concentration of chlorine dioxide required for the cycle, then instructs the module to produce that level of gas within the chamber. The module generates the gas by sending 1-4% chlorine gas through CD Cartridges which generate 2-8% chlorine gas. This gas is sent through compatible tubing or piping and flows into the chamber. The module includes sample pumps and tubing that pull gas from the chamber and into the module's photometer. The HMI and PCS also trigger the vacuum pump on the sterilizer to pull vacuum to achieve different pressure levels at selected times within the chamber. Built into the system is the ability to use the concentration level determined by the photometer to calculate the accumulated dosage and express it in the measure of ppm-hours. Once the load within the chamber reaches that dosage and the sterilization process has been achieved, the system will automatically initiate aeration and the removal of the chlorine dioxide gas.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENT

Figure 1:
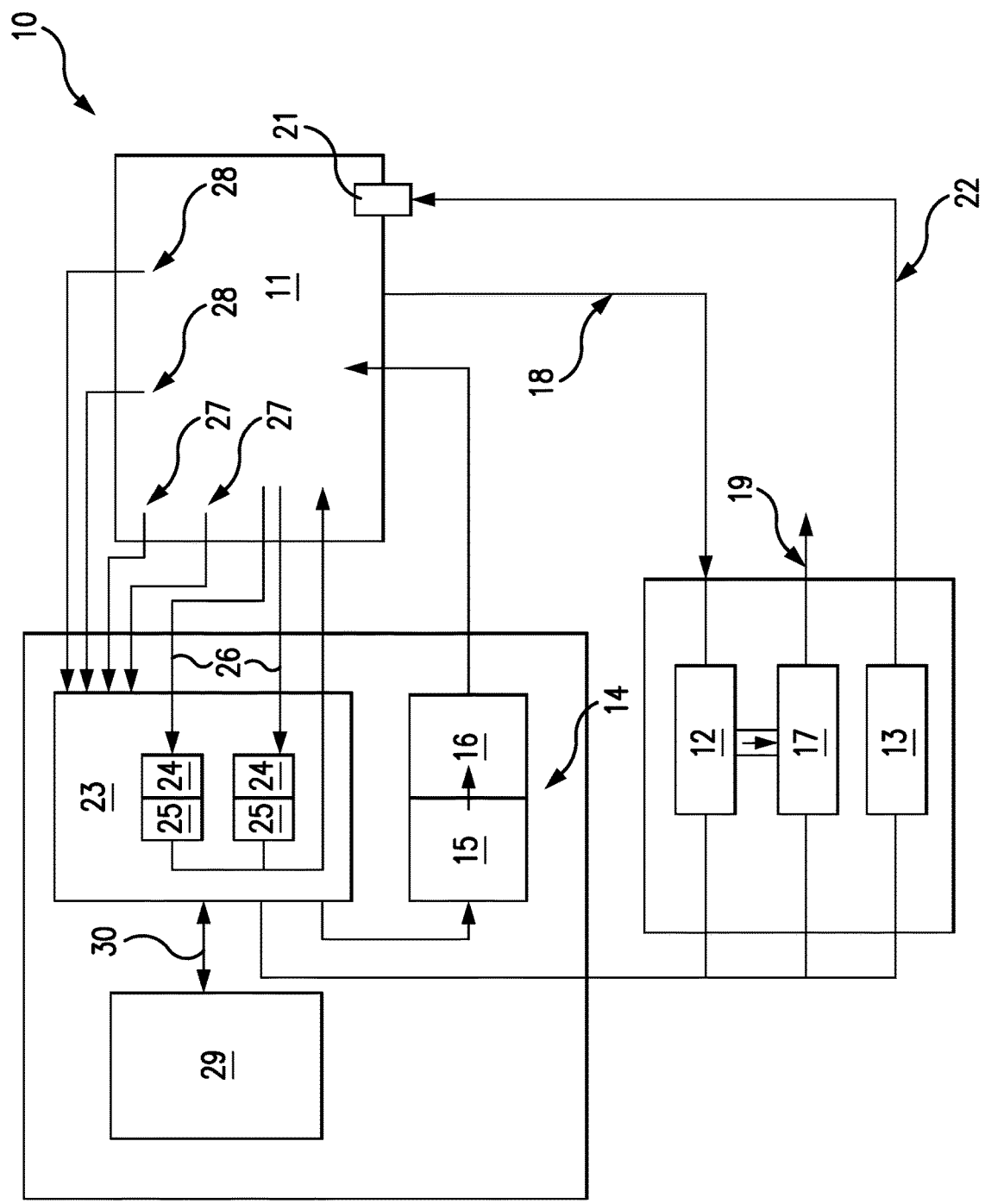
FIG. 1 is a schematic diagram of an exemplary embodiment of the present invention.

FIG. 1 depicts an exemplary embodiment of the present invention 10. The system 10 converts an existing ethylene oxide (EO) vacuum sterilizer into a chlorine dioxide (CD) vacuum sterilizer. In so doing, the system 10 repurposes certain components of the EO sterilizer, including the EO vacuum sterilization chamber 11 and, optionally, the vacuum pump 12 and/or the steam generator 13.

A CD generator 14 pneumatically communicates with the chamber interior 11 and comprises a source of chlorine gas 15 and multiple CD cartridges 16 which convert the chlorine gas to CD gas and inject the CD gas into the chamber interior 11 at a controlled rate corresponding to a selected CD concentration. In this exemplary embodiment 10, the CD cartridges 16 contain sodium chlorite, which chemically reacts with the chlorine gas 15 to produce CD.

A vacuum pump 12, which can be repurposed from the existing EO sterilizer, pneumatically communicates with the chamber interior 11 and creates therein a partial vacuum of a selected sterilization pressure. The vacuum pump 12 also serves to evacuate the chamber interior 11 after the sterilization process is complete, and to pump the evacuated gas 18 out of the chamber interior 11 and into a scrubber 17. The scrubber 17, in turn, removes residual CD gas from the evacuated gas 18 and exhausts the scrubbed air flow 19 into the outside atmosphere. In this exemplary embodiment 11, the scrubber 17 utilizes activated carbon to remove residual CD gas from the evacuated gas 18.

A steam generator 13 pneumatically communicates with the chamber interior 11 through a steam injection port 21, and it injects a controlled flow of steam 22 into the chamber interior 11 in accordance with a selected sterilization relative humidity and a selected sterilization temperature.

A process control system 23 comprises multiple sensors that continuously monitor multiple process conditions within the chamber 11. In this embodiment 10, there are two CD sensors 24, which monitor CD concentration within the chamber 11. Each of the CD sensors 24 is equipped with a CD sensor pump 25, which pulls a gas sample 26 from the chamber 11 into the CD sensor 24 and pumps the gas sample 26 back into the chamber 11. In this embodiment 10, there are also two Pressure/Temperature (PT) sensors 27 and two Relative Humidity (RH) sensors 28, which monitor, respectively the vacuum pressure, temperature, and relative humidity within the chamber 11.

Based on the readings of the process conditions by the sensors, the process control system 23 controls the CD generator 14, the vacuum pump 12 and steam generator 13 to produce within the chamber 11 the selected levels for CD concentration, sterilization pressure, sterilization temperature, and sterilization relative humidity and to maintain within the chamber 11 those selected levels for a selected sterilization duration based on a selected accumulated CD dosage. At the conclusion of the selected sterilization duration, the process control system 23 controls the vacuum pump 12 and the scrubber 17 to evacuate the chamber interior 11, remove residual CD gas from the evacuated gas 18, and exhaust the scrubbed airflow 19 to an outside atmosphere.

A Human-Machine Interface (HMI) receives user inputs that specify the sterilization process parameters 30, comprising the selected CD concentration, the selected sterilization pressure, the selected sterilization temperature, the selected sterilization relative humidity, and the selected sterilization duration based on the accumulated CD dosage. The HMI 29 transmits the sterilization process parameters 30 to the process control system 23 for implementation.

The sterilization process parameters 30 are determined based on characteristics of the "load," i.e., the medical device and its packaging, if any, to be sterilized, which characteristics can include: physical and chemical composition, gas permeability, bacterial endotoxins present, concentration of bacterial endotoxins present, the bioburden, and the resistance values determined by an External Process Challenge Device (EPCD).

Figure 2:
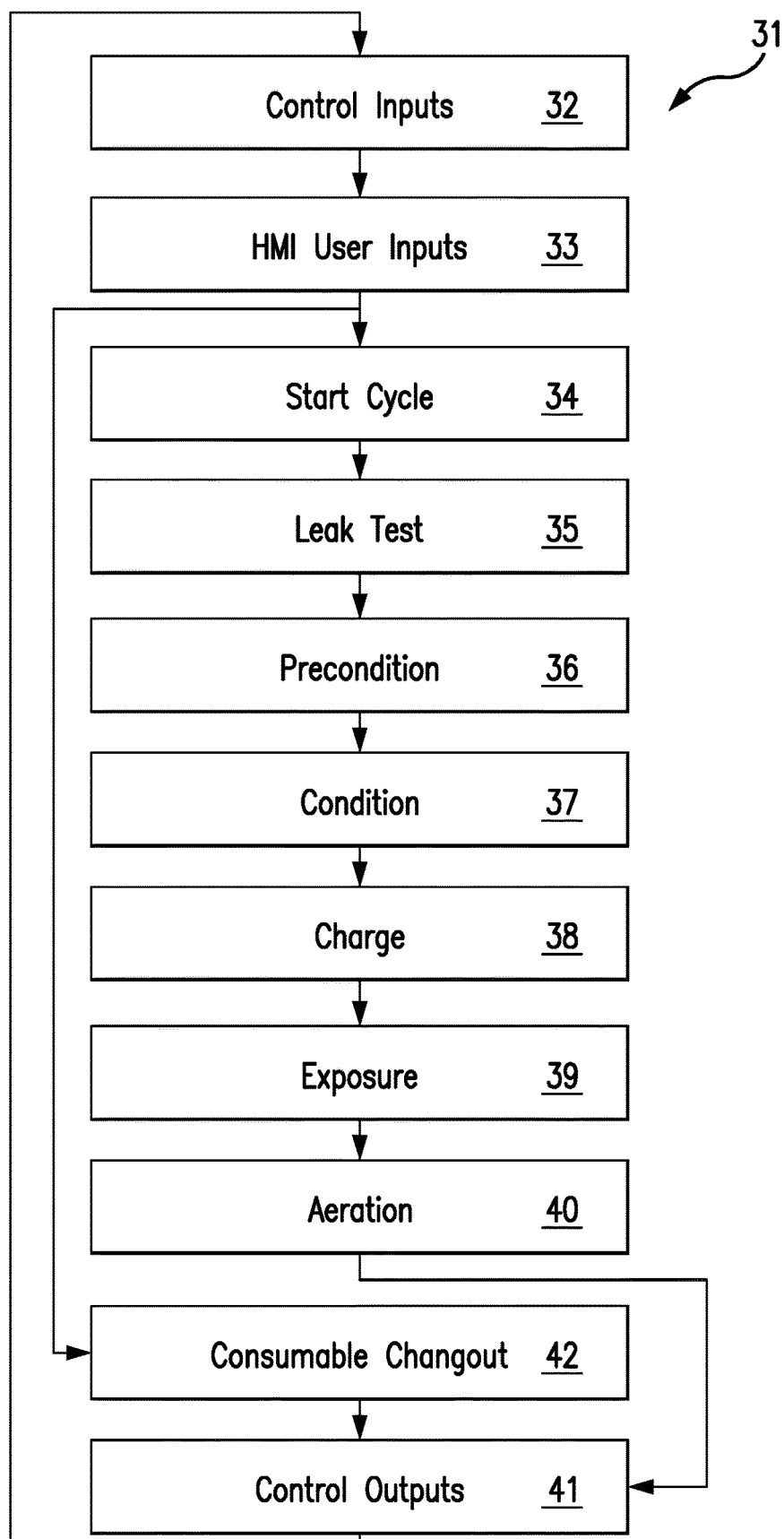
FIG. 2 is a flow chart of an exemplary sterilization cycle executed by the present invention.

Referring to FIG. 2, an exemplary sterilization cycle 31 executed by the present invention is illustrated. Control Inputs 32 are generated by the process control system 23, based on readings of the process conditions by the sensors 24 27 28. User Inputs 33 through the HMI 29 establish the selected sterilization process parameters 30, which initiates the start of the cycle 34. The chamber 11 is then pressurized and tested during the Leak Test 35, and the chamber's RH is raised to the setpoint 36, so as to condition the load 37. During the charge 38 phase of the Cycle, the CD concentration is raised to the setpoint, and then the load is exposed 39 to that concentration for the selected duration based on the selected accumulated CD dosage. During the Aeration phase 40, residual CD gas 18 is removed from the chamber 11, as controlled by outputs 41 from the process control system 23. Before initiation of a new Cycle, consumed supplies of chlorine gas 15 and CD cartridges 16 are replenished 42, to the extent necessary.

Although the preferred embodiment of the present invention has been disclosed for illustrative purposes, those skilled in the art will appreciate that many additions, modifications and substitutions are possible, without departing from the scope and spirit of the present invention as defined by the accompanying claims.

What is claimed is:

1. A system for converting an existing ethylene oxide vacuum sterilizer into a chlorine dioxide vacuum sterilizer, the system comprising:
    an ethylene oxide vacuum sterilization chamber, having a chamber interior, wherein the ethylene oxide vacuum sterilization chamber is a component of the existing ethylene oxide vacuum sterilizer;
    a chlorine dioxide generator, which pneumatically communicates with the chamber interior, wherein the chlorine dioxide generator comprises a source of a chlorine gas and at least one cartridge that is configured to chemically convert the chlorine gas into a chlorine dioxide gas and to inject the chlorine dioxide gas into the chamber interior at a controlled rate corresponding to a selected chlorine dioxide concentration in the chamber interior;
    a vacuum pump, which pneumatically communicates with the chamber interior, wherein the vacuum pump is configured to create and control a partial vacuum of a selected sterilization pressure within the chamber interior, and wherein the vacuum pump is configured to effect a controlled post-sterilization evacuation of the chamber interior and to pump an evacuated gas out of the chamber interior;
    a steam generator, which pneumatically communicates with the chamber interior through a steam injection port, wherein the steam generator is configured to inject a controlled flow of steam into the chamber interior, as determined by a selected sterilization relative humidity within the chamber interior;
    a process control system, comprising multiple sensors configured to monitor multiple process conditions within the chamber interior, wherein the process conditions comprise chlorine dioxide concentration, vacuum pressure, relative humidity, and temperature, and wherein, based on readings of the process conditions by the sensors, the process control system is configured to control the chlorine dioxide generator, the vacuum pump and the steam generator to produce and maintain within the chamber the selected chlorine dioxide concentration, the selected sterilization pressure, the selected sterilization relative humidity, and a selected sterilization temperature, for a selected sterilization duration based on a measured or estimated accumulated chlorine dioxide dosage, and wherein, at the conclusion of the selected sterilization duration, the process control system is configured to control the vacuum pump to evacuate the chamber interior; and
    a human-machine interface, which is configured to receive user inputs that specify multiple sterilization process parameters, comprising the selected chlorine dioxide concentration, the selected sterilization pressure, the selected sterilization relative humidity, the selected sterilization temperature, and the selected sterilization duration based on the measured or estimated accumulated chlorine dioxide dosage, wherein the human-machine interface is configured to transmit the sterilization process parameters to the process control system.

2. The system according to claim 1, further comprising a scrubber, which pneumatically communicates with the vacuum pump, wherein, at the conclusion of the selected sterilization duration, the process control system is configured to control the vacuum pump to evacuate the chamber interior into the scrubber, and to control the scrubber to remove a post-sterilization residual chlorine dioxide gas from the evacuated gas and to exhaust a scrubbed airflow into an ambient atmosphere.

3. The system according to claim 1, wherein the vacuum pump or the steam generator, or both the vacuum pump and the steam generator, are components of the existing ethylene oxide vacuum sterilizer.

4. The system according to claim 2, wherein the vacuum pump or the steam generator, or both the vacuum pump and the steam generator, are components of the existing ethylene oxide vacuum sterilizer.

5. The system according to claim 2, wherein the scrubber utilizes activated carbon to remove the post-sterilization residual chlorine dioxide gas from the evacuated gas.

6. The system according to claim 4, wherein the scrubber utilizes activated carbon to remove the post-sterilization residual chlorine dioxide gas from the evacuated gas.

7. The system according to claim 1, wherein the sterilization process parameters are determined based on characteristics of a medical device to be sterilized selected from the group consisting of: composition of the medical device, including device packaging if any, gas permeability of the medical device, including device packaging if any, types of bacterial endotoxins present in the medical device, a concentration of bacterial endotoxins present in the medical device, a bioburden of the medical device, and a sterilization resistance valve determined by an External Process Challenge Device.

8. The system according to claim 2, wherein the sterilization process parameters are determined based on characteristics of a medical device to be sterilized selected from the group consisting of: composition of the medical device, including device packaging if any, gas permeability of the medical device, including device packaging if any, types of bacterial endotoxins present in the medical device, a concentration of bacterial endotoxins present in the medical device, a bioburden of the medical device, and a sterilization resistance valve determined by an External Process Challenge Device.

9. The system according to claim 3, wherein the sterilization process parameters are determined based on characteristics of a medical device to be sterilized selected from the group consisting of: composition of the medical device, including device packaging if any, gas permeability of the medical device, including device packaging if any, types of bacterial endotoxins present in the medical device, a concentration of bacterial endotoxins present in the medical device, a bioburden of the medical device, and a sterilization resistance valve determined by an External Process Challenge Device.

10. The system according to claim 4, wherein the sterilization process parameters are determined based on characteristics of a medical device to be sterilized selected from the group consisting of: composition of the medical device, including device packaging if any, gas permeability of the medical device, including device packaging if any, types of bacterial endotoxins present in the medical device, a concentration of bacterial endotoxins present in the medical device, a bioburden of the medical device, and a sterilization resistance valve determined by an External Process Challenge Device.

11. The system according to claim 5, wherein the sterilization process parameters are determined based on characteristics of a medical device to be sterilized selected from the group consisting of: composition of the medical device, including device packaging if any, gas permeability of the medical device, including device packaging if any, types of bacterial endotoxins present in the medical device, a concentration of bacterial endotoxins present in the medical device, a bioburden of the medical device, and a sterilization resistance valve determined by an External Process Challenge Device.

12. The system according to claim 6, wherein the sterilization process parameters are determined based on characteristics of a medical device to be sterilized selected from the group consisting of: composition of the medical device, including device packaging if any, gas permeability of the medical device, including device packaging if any, types of bacterial endotoxins present in the medical device, a concentration of bacterial endotoxins present in the medical device, a bioburden of the medical device, and a sterilization resistance valve determined by an External Process Challenge Device.

* * * * *